(12) United States Patent
Clark et al.

(10) Patent No.: US 10,189,053 B2
(45) Date of Patent: Jan. 29, 2019

(54) CURVED ULTRASONIC HIFU TRANSDUCER WITH PRE-FORMED SPHERICAL MATCHING LAYER

(75) Inventors: Dennis Dean Clark, Lewistown, PA (US); Barry C. Scheirer, McAlisterville, PA (US); Ryan Manning, Lewistown, PA (US); Haifeng Wang, State College, PA (US)

(73) Assignee: Koninklijke Philips N.V., Eindhoven (NL)

( * ) Notice: Subject to any disclaimer, the term of this patent is extended or adjusted under 35 U.S.C. 154(b) by 759 days.

(21) Appl. No.: 13/508,709

(22) PCT Filed: Nov. 3, 2010

(86) PCT No.: PCT/IB2010/054982
§ 371 (c)(1),
(2), (4) Date: May 8, 2012

(87) PCT Pub. No.: WO2011/055313
PCT Pub. Date: May 12, 2011

(65) Prior Publication Data
US 2012/0226201 A1 Sep. 6, 2012

Related U.S. Application Data

(60) Provisional application No. 61/259,301, filed on Nov. 9, 2009.

(51) Int. Cl.
*B06B 1/06* (2006.01)
*G10K 11/02* (2006.01)
*A61N 7/02* (2006.01)

(52) U.S. Cl.
CPC ............ *B06B 1/0637* (2013.01); *G10K 11/02* (2013.01); *A61N 7/02* (2013.01)

(58) Field of Classification Search
USPC .......................................... 600/437
See application file for complete search history.

(56) References Cited

U.S. PATENT DOCUMENTS

| 3,732,535 A | 5/1973 | Ehrlich |
| 4,992,692 A | 2/1991 | Fleming |

(Continued)

FOREIGN PATENT DOCUMENTS

| CN | 1257414 A | 6/2006 |
| CN | 101242872 A | 8/2008 |

(Continued)

OTHER PUBLICATIONS

"A Linear Phased Array for Prostate Therapy" Bechtold et al, IEEE Ultrasonics Symposium 1997 vol. 2, Oct. 5-8, 1997 p. 1385-1388.

*Primary Examiner* — Tse Chen
*Assistant Examiner* — Jason Ip (57) ABSTRACT

A curved high intensity focused ultrasound (HIFU) transducer comprising a curved piezoelectric array having opposite convex and concave surfaces, the concave surface being a transmitting surface, and a plurality of acoustic transmission areas, a plurality of electrodes located on the surfaces of the curved piezoelectric array for applying electrical transmit signals to the acoustic transmission areas, and a unitary, continuously formed curved matching layer preformed to the desired curvature of the curved transducer array and bonded to the transmitting surface of the curved piezoelectric array which provides acoustic matching and electrical isolation for the transmitting surface of the curved piezoelectric array.

20 Claims, 8 Drawing Sheets

(56) References Cited

U.S. PATENT DOCUMENTS

| | | | |
|---|---|---|---|
| 5,423,220 A * | 6/1995 | Finsterwald et al. | 73/642 |
| 5,438,999 A * | 8/1995 | Kikuchi | G10K 11/32 310/336 |
| 5,637,800 A * | 6/1997 | Finsterwald et al. | 73/642 |
| 5,743,862 A | 4/1998 | Mamoru | |
| 6,050,943 A * | 4/2000 | Slayton et al. | 600/439 |
| 6,128,522 A | 10/2000 | Acker et al. | |
| 6,516,211 B1 | 2/2003 | Acker et al. | |
| 6,602,197 B2 | 8/2003 | Tahara | |
| 6,773,408 B1 | 8/2004 | Acker et al. | |
| 7,117,588 B2 | 10/2006 | Vafi | |
| 2003/0017101 A1 | 1/2003 | Klett | |
| 2003/0018267 A1* | 1/2003 | Erikson et al. | 600/459 |
| 2003/0171700 A1* | 9/2003 | Martin et al. | 601/2 |
| 2006/0058678 A1 | 3/2006 | Vitek et al. | |
| 2007/0016039 A1 | 1/2007 | Vortman et al. | |
| 2007/0167803 A1 | 7/2007 | Kaminskyi | |
| 2009/0088623 A1 | 4/2009 | Vortman et al. | |
| 2009/0099483 A1 | 4/2009 | Rybyants | |
| 2009/0230820 A1 | 9/2009 | Nudelman et al. | |
| 2009/0230822 A1* | 9/2009 | Kushculey et al. | 310/366 |
| 2009/0230823 A1 | 9/2009 | Kushculey et al. | |

FOREIGN PATENT DOCUMENTS

| | | |
|---|---|---|
| EP | 0998217 A1 | 5/2000 |
| EP | 1832314 A1 | 9/2007 |
| JP | 04227247 A | 8/1992 |
| JP | 2004512856 A | 4/2004 |
| JP | 2005517488 A | 6/2005 |
| WO | 9852465 A1 | 11/1998 |
| WO | 2000057495 A1 | 9/2000 |
| WO | 02063606 | 8/2002 |
| WO | 02063606 A1 | 9/2002 |
| WO | 2007035529 | 3/2007 |
| WO | 2008003910 A1 | 1/2008 |
| WO | 2009055725 | 4/2009 |

* cited by examiner

CURVED ULTRASONIC HIFU TRANSDUCER WITH PRE-FORMED SPHERICAL MATCHING LAYER

This invention relates to medical diagnostic ultrasound systems and, in particular, to ultrasonic transducers which are used for controlled heating of body tissues by high intensity focused ultrasound, known as HIFU.

Ultrasonically delivered elevated temperature treatments are used for a variety of therapeutic purposes In HIFU treatment, ultrasonic energy is focused to a small spot within the body so as to heat the tissues to a temperature sufficient to create a desired therapeutic effect. The technique is similar to lithotripsy, where focused energy is high enough to break up kidney stones, but with considerably less energy that is delivered over an extended time rather than a sudden pulse. The HIFU technique can be used to selectively destroy unwanted tissue within the body. For example, tumors or other pathological tissues can be destroyed by applying focused ultrasonic energy so as to heat the cells to a temperature sufficient to kill the tissue, generally about 60 to about 80 degrees C., without destroying adjacent normal tissues. Other elevated-temperature treatments include selectively heating tissues so as to selectively activate a drug or to promote some other physiological change in a selected portion of the subject's body.

HIFU transducers are often formed as spherical or parabolic dishes with a radius of curvature that gives the transducer a geometric focal point. See, for example, the HIFU transducer described in international patent application publication number WO 98/52465 (Acker et al.) The transducer described in this publication is formed by a number of transducer sections secured to a frame with the desired curvature. When the individual sections or transducer elements in the sections can be individually energized with drive signals of different phases and amplitudes, the entire transducer can be steered and focused in the manner of a phased array to steer the focal point of the energy around the nominal geometric focus.

A significant number of transducer sections are needed to provide the high energy to be delivered by the transducer. The transducer of the Acker et al. publication is about 15 cm in diameter and has many transducer sections attached to its dish-shaped frame. Accurate placement of the transducer sections on the frame is needed to give the final assembly its desired spherical shape and acoustical properties. This poses a significant fabrication and construction effort and requires painstaking quality control and testing to verify that each section is fully operational. Accordingly it would be desirable to provide a transducer structure that can be more easily formed into its desired shape, and preferably using components which play a role in the acoustic performance of the spherical transducer.

In accordance with the principles of the present invention, a spherical HIFU transducer is described which is formed of a plurality of composite ceramic piezoelectric tiles fitted around a pre-formed spherical matching layer. The matching layer is separately formed in advance of assembly of the transducer with the piezoelectric tiles then using the matching layer as a form for assembly of the spherical transducer. The matching layer is formed as a continuous body which provides electrical and environmental isolation between the piezoelectric elements and the front emitting side of the transducer.

Construction of a HIFU transducer of the present invention may begin with fabrication of a spherical or dish-shaped matching layer. The matching layer(s) of a transducer provide at least a partial matching of the acoustic properties of the piezoelectric transducer to the acoustic properties of the patient's body or the medium between the transducer and the patient. The properties matched may include acoustic impedance, velocity of sound, and material density. In the conventional construction of an ultrasound transducer the matching layer is generally formed on the transducer stack and is formed over the reference electrodes on the emitting surface of the piezoelectric material. For the HIFU transducer described in this disclosure a spherical matching layer is formed by itself, separate from the rest of the transducer. There are several ways to form the spherical matching layer, including casting, molding, thermoforming, or machining. The spherical matching layer of the HIFU transducer described herein is made of a loaded epoxy which is loaded with particles which provide the matching layer with its desired acoustic properties as is known in the art. Preferably the particles are non-magnetic. In casting or molding the spherical matching layer, the loaded epoxy is poured into a concave fixture of the desired spherical shape. A convex fixture is closed over the concave fixture, forcing the liquid epoxy to fill the spherical space between the two fixtures.

Figure 1:
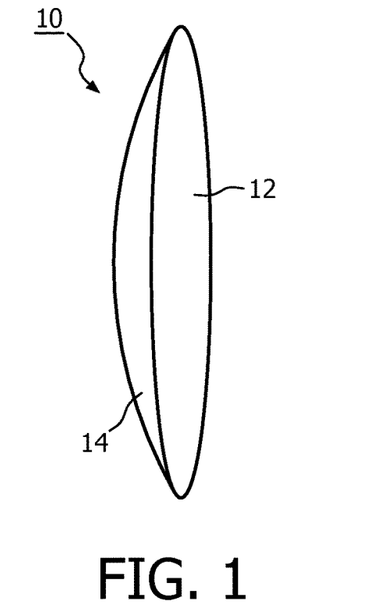
FIG. 1 illustrates in perspective a spherical transducer matching layer separately formed for a HIFU transducer of the present invention.

The epoxy is cured and removed from the fixtures, then peripherally machined to its final form. In a thermoform process a planar sheet of the desired thickness is formed of the loaded epoxy, then partially cured. The sheet is then placed over a heated convex or concave fixture of the desired curvature which warms the sheet so that it becomes pliant and conforms to the curvature of the fixture. When the sheet has attained its desired spherical shape it is cured and finished. In a machining process a disk of loaded epoxy is cast or molded and cured. The disk is then machined on one side to form a convex surface. The disk is then put on a concave fixture and the other side of the disk is machined to form the concave side of the spherical matching layer. In a constructed embodiment the finished spherical matching layer from any of these processes is 0.5 mm thick, has a diameter of 140 mm, and a spherical radius of 140 mm, the size and shape of the finished HIFU transducer. FIG. 1 illustrates such a spherical matching layer 10. The concave surface 12 is the emitting surface of the finished transducer which faces the patient and the convex surface 14 is sputtered to produce a redundant signal return electrode, then covered with composite piezoelectric tiles. The rigid matching layer thus provides a form of the desired curvature for assembly of the piezoelectric tile layer. Since the matching layer 10 in front of the tiles is a continuously formed surface, it provides the desired electrical and moisture-impervious environmental isolation of the electrical elements of the HIFU transducer from the patient and the external surroundings in front of the HIFU transducer.

Figure 2A:
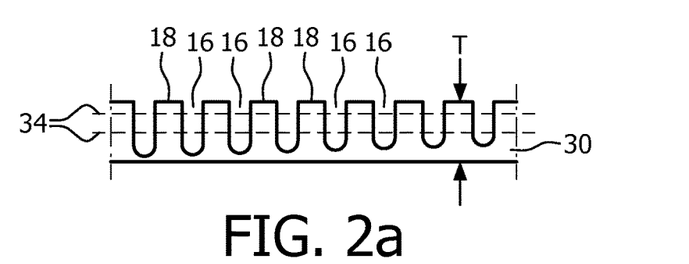
FIG. 2a illustrates an end view of a sheet of ceramic piezoelectric material which has been diced to form a composite transducer array for a HIFU transducer of the present invention.
Figure 2B:
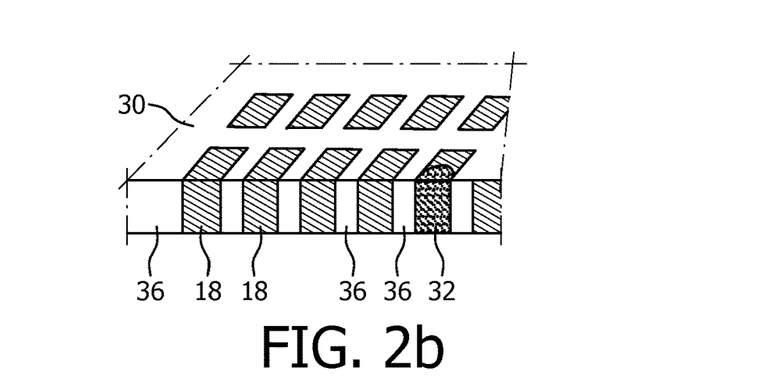
FIG. 2b illustrates a composite transducer array with a nonmagnetic via constructed in accordance with the principles of the present invention.

Construction of the composite piezoelectric transducer array begins with a sheet 30 of ceramic piezoelectric material as shown in FIGS. 2a and 2b. In a constructed transducer the sheet 30 is 1.2 mm thick (T). First, a number of holes are drilled through the sheet 30 where it is desired to have electrical connections from the back to the front (emitting side) of the transducer. The holes are then filled with silver-filled epoxy to form vias 32 through the sheet. The silver filling provides electrical conductivity and is non-magnetic for operation in a magnetic field of an MRI system. Other non-magnetic conductive material may be used for the conductive filling. The silver epoxy is cured. The sheet is then diced part-way through the thickness with parallel cuts 16 in one direction as shown in the view of the edge of the sheet 30 in FIG. 2a. Then the sheet is diced part-way through with parallel cuts in the orthogonal direction, leaving a plurality of upward projecting piezoelectric posts 18 and vias 32. The dicing cuts are then filled with non-conducting epoxy and cured. The top and bottom surfaces of the sheet are then machined flat to the depths indicated by dashed lines 34 in FIG. 2a. This will result in a finished sheet of a matrix of piezoelectric posts 18 and conductive vias 32 in epoxy 36 as shown in FIG. 2b. The finished sheet comprises a 1:3 matrix of piezoelectric posts, each of which has its dominant vibrational mode in its longitudinal direction through the thickness of the sheet, and which transmits ultrasound predominately in a direction toward the front (patient facing) side of the transducer. This predominant vibrational mode of the composite material reduces unwanted lateral transmission across the array to other active areas of the array.

Figure 4:
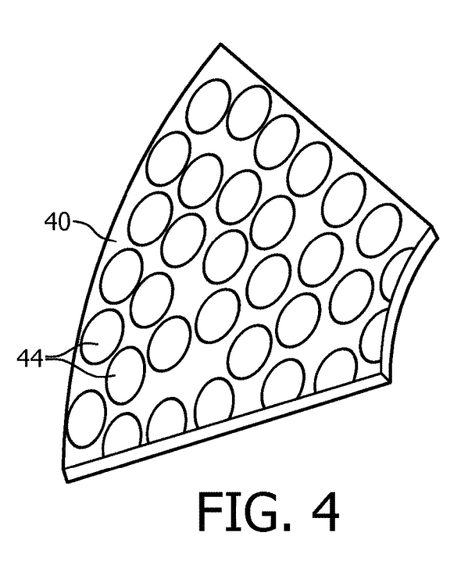
FIG. 4 illustrates a composite piezoelectric tile prior to spherical shaping for a HIFU transducer of the present invention.

The flat composite piezoelectric sheet 30 is machined to a trapezoidal shape as shown by the peripheral shape of the composite piezoelectric tile 40 of FIG. 4. In a constructed HIFU transducer the tiles have the trapezoidal shape of FIG. 4 to allow for a circular spherical center tile as described below. Alternatively, each tile may be machined in the shape of a slice of pie, so that the tiles will cover the matching layer without need for a center tile. The tiles could also take on other geometric shapes arranged to cover the spherical surface including but not limited to pentagons mixed with hexagons as demonstrated by the panels of a soccer ball. The flat trapezoidal tile of FIG. 4 is then given its desired spherical curvature. Since the composite transducer is formed of a matrix in epoxy, the tile can be heated to soften the epoxy so that the tile can be conformed to the desired curvature. This can be done by placing the tile 40 on a heated concave or convex fixture, then pressing the tile into conformance with the convex or concave shape. While the tile is held in the desired curvature, the fixture is cooled and the epoxy is allowed to fully cure. The result is a spherical-shaped composite piezoelectric tile for a spherical HIFU transducer.

Figure 3:
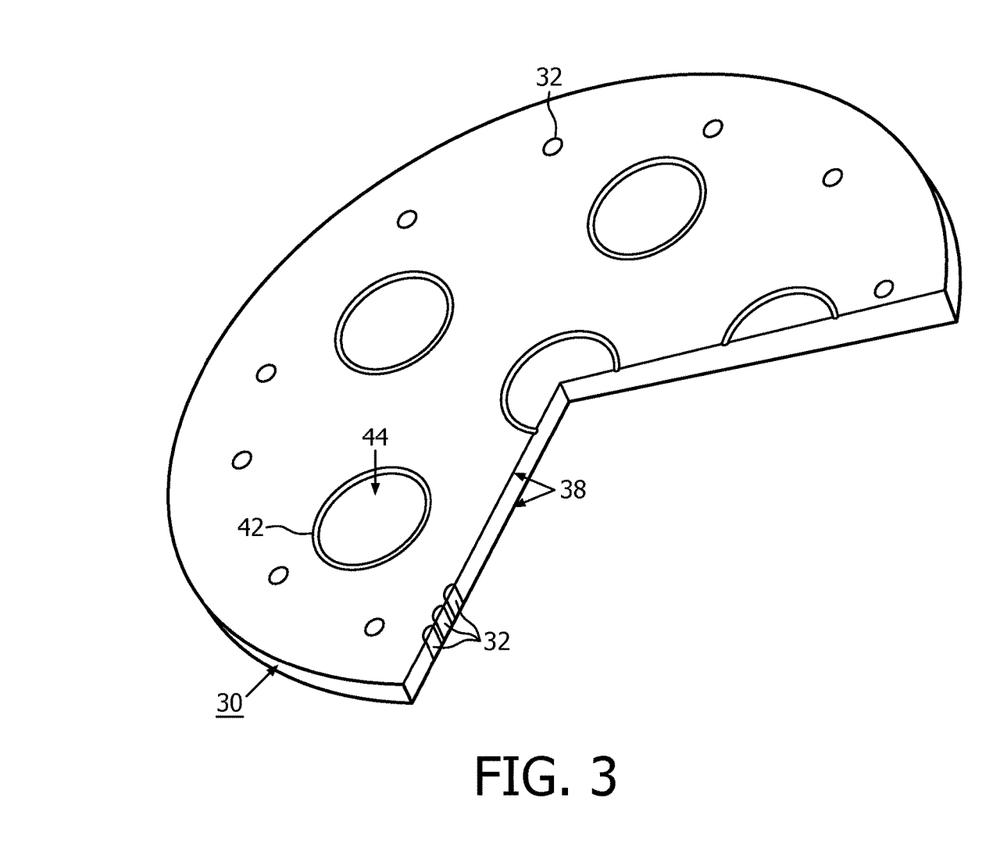
FIG. 3 illustrates a composite transducer array with emitting elements and nonmagnetic vias constructed in accordance with the principles of the present invention.

After the tile has been curved the top and bottom surfaces 38 are metallized by sputtering a conductive material onto the surfaces of the sheet as shown for the sheet 30 of FIG. 3. Preferably the conductive material is non-magnetic such as gold or titanium/gold. The metallized surfaces are electrically connected by the conductive vias 32, providing electrical connection from the back surface of the composite sheet to the front. Active (transmitting and receiving) areas of the composite piezoelectric sheet are then isolated by diamond core drilling, laser drilling, or ultrasonic machining around desired active areas from the back (convex) surface of the tile. Several such defined active areas 44 are shown in FIGS. 3 and 4. The cuts 42 which define the active areas cut through the metallization of the surface of the sheet to electrically isolate the areas and preferably extend over half-way through the composite sheet so as to acoustically isolate the active area from the surrounding areas of the sheet and other active areas. Alternatively, the active areas can be electrically and acoustically isolated after the tiles are bonded to the matching layer.

In a constructed tile the active areas 44 are not symmetrically arranged in rows or columns or circles or other regular patterns but are irregularly or randomly arranged as shown in FIG. 4. The random pattern prevents any significant additive combining of the acoustic sidelobes of the active areas which would diminish the effective energy delivered by the HIFU transducer.

Figure 5:
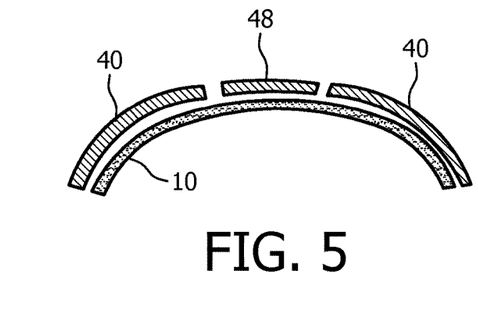
FIG. 5 illustrates in cross-section the placement of composite piezoelectric tiles on the matching layer for a HIFU transducer of the present invention.

Eight of the spherical trapezoidal tiles 40 are then thin bonded adjacent to each other around the convex surface 14 of the matching layer 10, which thereby provides a form for assembly of the tiles. If the spherical tiles 40 are pie-shaped as described above, the tiles will completely cover the convex side of the matching layer 10. When the spherical tiles are trapezoidal as shown in FIG. 4, they will cover the convex side of the matching layer except for the center of the matching layer. This circular spherical space can be left open. Alternatively it can be covered with a circular spherical thermal conductor such as aluminum for cooling. Returning acoustic energy will tend to be focused in the center of the HIFU transducer by virtue of its spherical geometric shape. Locating a thermal conductor here can aid in cooling the HIFU transducer. Alternatively, a circular spherical composite piezoelectric tile 48 can fill this space. For example, the circular sheet of FIG. 3, with its own active areas, can be formed into a spherical shape and located here, providing full composite piezoelectric coverage of the matching layer 10 as shown by the cross-sectional view of the trapezoidal and circular tiles on the matching layer 10 in FIG. 5. In a constructed transducer of this full coverage design, the nine tiles provide the HIFU transducer with 265 active areas, 256 for transmit and nine for receive.

It is seen in FIG. 3 that the vias 32 are located so as to connect the metallized area around the active areas on the back surface to the metallized surface on the front (patient-facing) side of the tile. In a constructed HIFU transducer the metallized area around the active areas 44 is electrically coupled to a reference potential. The vias 32 couple this reference potential to the metallized surface on the other side of the tile, the side not visible in FIG. 3. The vias are thus used to apply a reference potential to the patient-facing side of the composite piezoelectric tiles, and also to the metallization on the patient-facing side of the active areas 44. Since the patient-facing side of the tiles 40 are bonded to the matching layer 10 and are thus inaccessible for electrical connections, the vias provide the needed electrical connection through the piezoelectric sheet to the front side of the tile.

Figure 6:
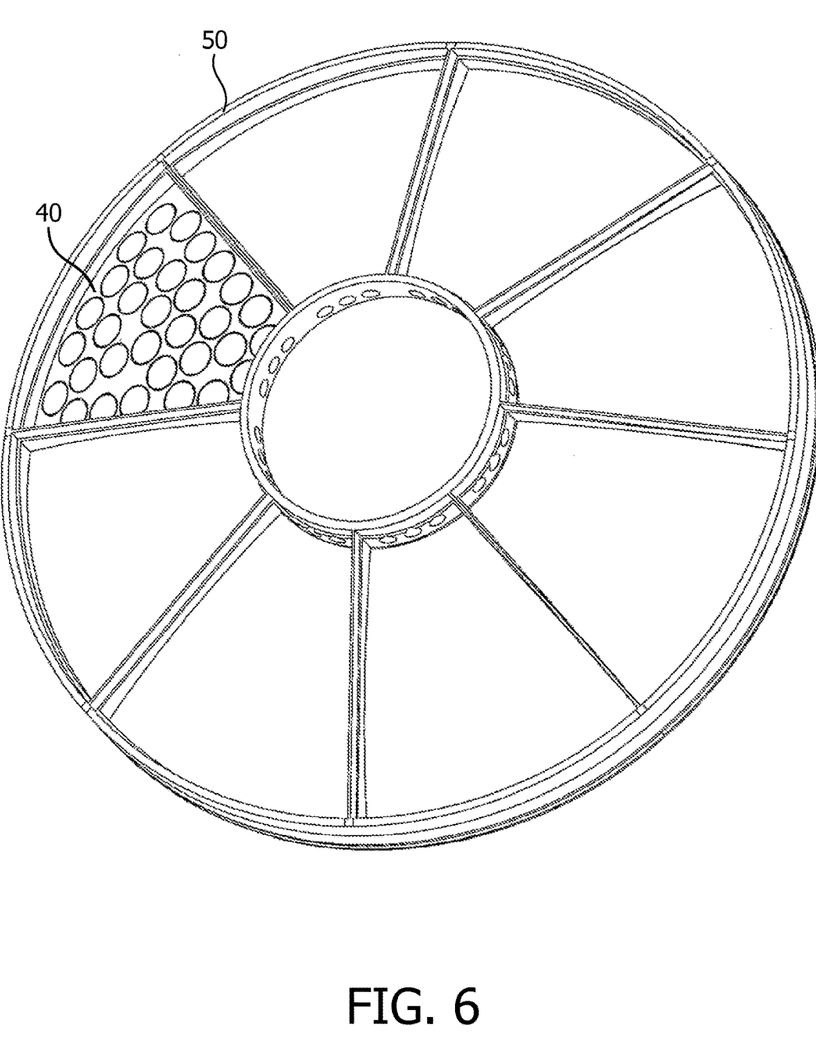
FIG. 6 illustrates in perspective the back of a nine-tile HIFU transducer of the present invention.
Figure 7A:
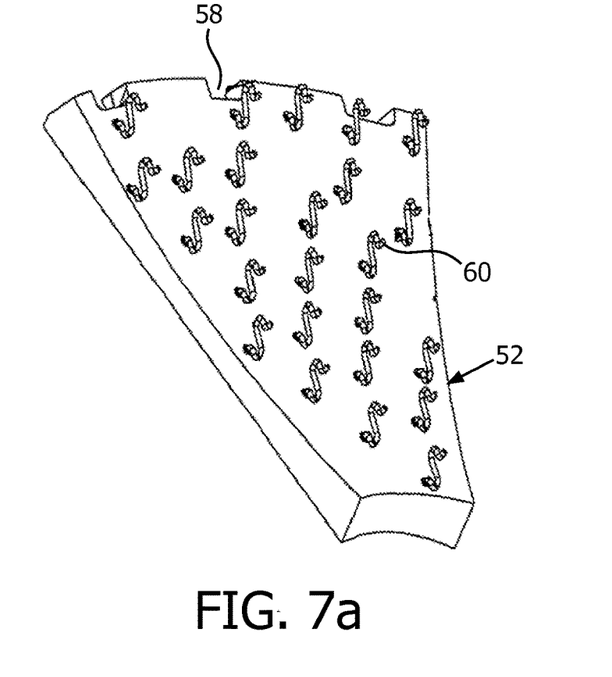
FIGS. 7a and 7b illustrate the front and back surfaces of a curved printed circuit board with extended compliant contacts for a HIFU transducer of the present invention.
Figure 7B:
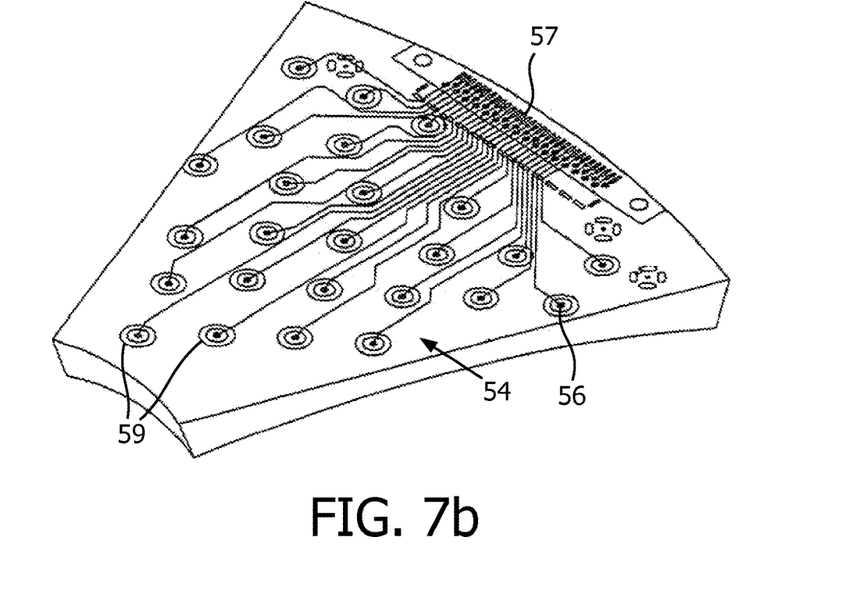

Next, a plastic support frame 50 is attached to the back of the assembled tiles by bonding, snap fit, or fasteners as shown in FIG. 6. In a constructed transducer each of the nine tiles 40,48 is accessible between the ribs of the support frame. The support frame is used to mount eight trapezoidal and one circular printed circuit boards 52 in a spaced relation above the back surfaces of the composite piezoelectric tiles 40. FIGS. 7a and 7b illustrate the front and back (54) surfaces of the trapezoidal printed circuit boards 52. Located on the back surface 54 are printed circuit connections 56 from a connector 57 which are connected by plated through-holes 59 through the board to active areas of the HIFU transducer. On the front surface of the printed circuit boards are compliant metallic contacts 60 which span the space between a printed circuit board and its tile and electrically connect the printed circuit connections to the active areas 44 and vias 32 of the opposing composite piezoelectric tile 40. Located at one edge of the printed circuit board 52 which is at the periphery of the HIFU transducer are cooling notches 58.

Figure 8:
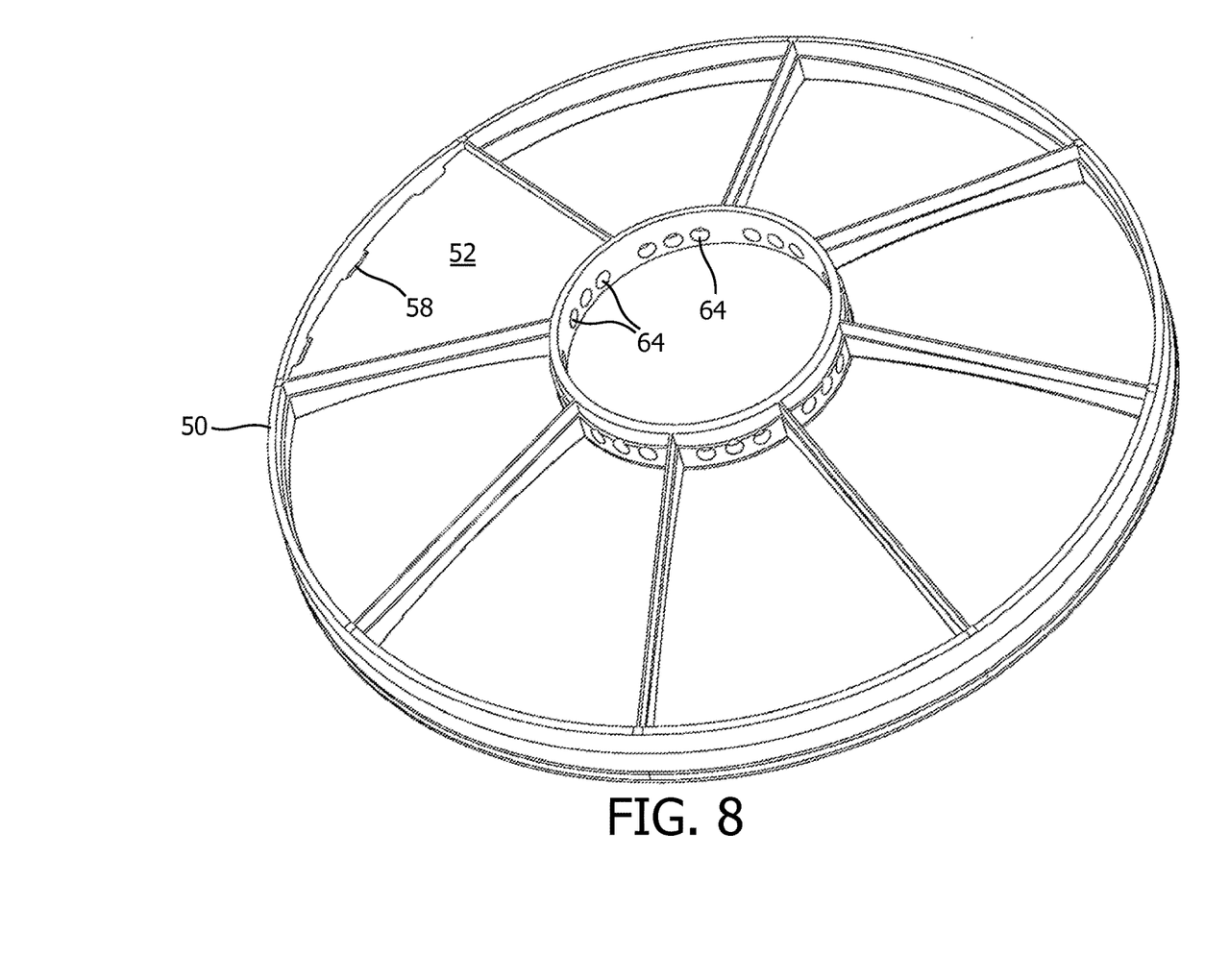
FIG. 8 illustrates in perspective the back of a HIFU transducer of the present invention with a support frame attached for the printed circuit boards of FIGS. 7a and 7b.

A printed circuit board 52 is bonded to the support frame 50 above each tile such as tile 40 shown in FIG. 6. When a printed circuit board is assembled in this manner it appears as shown by printed circuit board 52 in FIG. 8. Before this assembly, the extended ends of the compliant metallic contacts 60 are coated with conductive epoxy. When the printed circuit board is assembled on the frame, the ends of the contacts 60 will contact metallized areas of the opposing tile and become bonded in electrical connection with the metallized areas when the conductive epoxy cures. The contacts 60 thus provide electrical communication between the printed circuit boards and active and reference potential areas of the piezoelectric tiles.

While the printed circuit boards can be fabricated as conventional planar printed circuit boards, the printed circuit board 52 of FIGS. 7a and 7b preferably have a spherical curvature, matching that of the opposing composite piezoelectric tiles 40 to which they are connected by the contacts 60. The printed circuit boards can be curved on just the side facing the tile as shown in FIG. 7a, or on both sides. The printed circuit boards can be formed as curved boards in several ways. One is to start with a thick planar sheet of glass epoxy board material and machine or grind the surface of the board to the desired curvature. The other technique is to use thermoforming to heat the board material and soften the epoxy, then form the curvature by compressing the sheet against a fixture of the desired curvature. The circuit boards can be double-clad with photo-imaged and chemically-etched conductive lines on the top and bottom surfaces interconnected by plated through-holes formed in the boards. The circuit boards can also be multilayer boards with three or more layers of conductive lines formed on the surfaces and within layers of the board for more complex, higher density circuit configurations. The rigid boards 52 are also capable of securely mounting other electrical components such as the connector 57.

Figure 9:
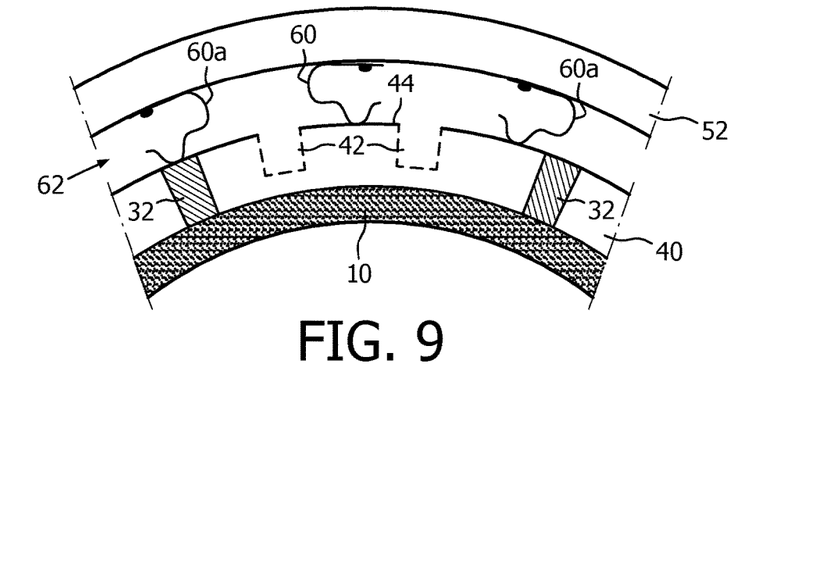
FIG. 9 is a detailed illustration of the connection of the extended compliant contacts of a printed circuit board to transducer areas of a HIFU transducer of the present invention.

The compliant metallic contacts 60 may be formed as springs, such as leaf springs, curled springs, or helical springs. The springs provide numerous benefits. First, they provide electrical connection from the printed circuit boards to provide drive signals and reference potential to areas of the piezoelectric of the HIFU transducer. When a flat, planar printed circuit board is used in opposition to a spherically shaped composite piezoelectric tile, the compliance of the contacts 60 will allow the contacts to span the uneven distance 62 between the board 52 and the piezoelectric tile, being relatively uncompressed when the spanned distance is greater and relatively more compressed when the distance is less. Second, they allow a space 62 to remain between the piezoelectric tiles which is used for cooling the piezoelectric tiles. Third, they provide compliant electrical connections which allow for the spacing between the printed circuit boards and the tiles to change with heating and cooling of the HIFU transducer. Fourth, since the metallic contacts are thermally conductive and span the air flow passageway between the piezoelectric material and the printed circuit board, they will conduct heat from the piezoelectric material which will be dissipated as air flows past the contacts in the passageway. These benefits can be appreciated from the enlarged view of these connections of FIG. 9. In this drawing the contacts 60 are formed as spring clips which span the cooling space 62 between the printed circuit board 52 and the tile 40. The center contact 60 is seen to be providing electrical connection to an active area 44 of the tile 40. This active transducer area 44 is isolated from the surrounding area of the tile by cuts 42 through the surface metallization and into the composite piezoelectric tile 40. On either side of the center contact 60 are spring clip contacts 60a which are connected to the metallization above vias 32. These electrical connections thereby connect the front metallized surface of the tile, that which is bonded to the matching layer 10 and is therefore inaccessible for direct electrical connection, to a desired electrical potential such as a reference potential.

Figure 10:
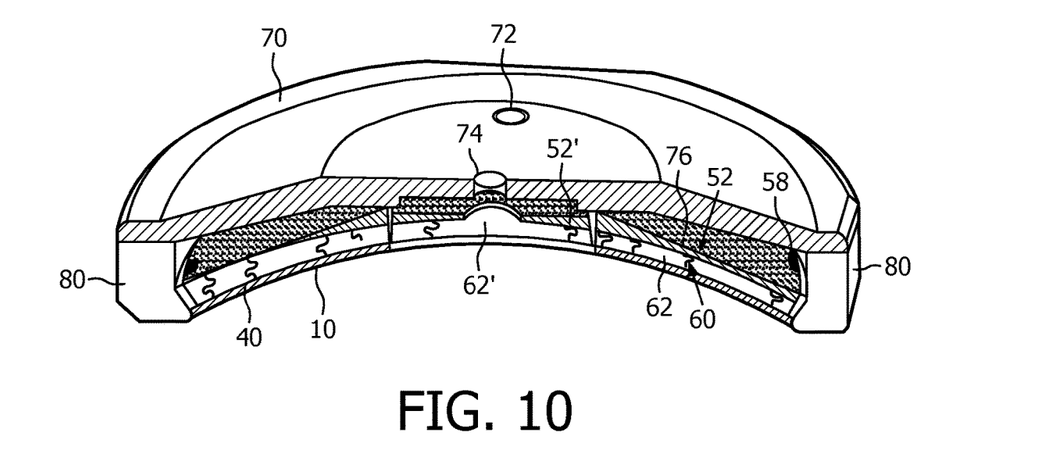
FIG. 10 is a partial cross-sectional and perspective view of a HIFU transducer of the present invention with a peripheral frame and back duct cover.
Figure 11:
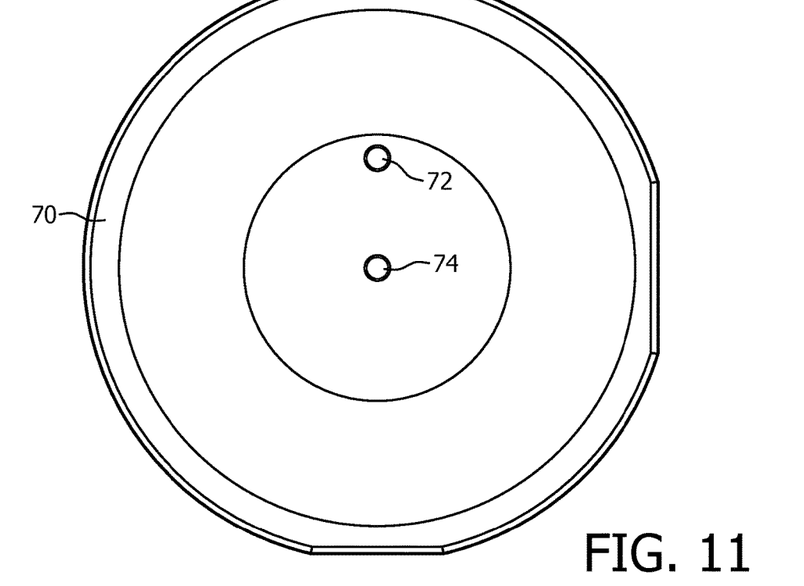
FIG. 11 is a plan view of the back duct cover of FIG. 10.

FIG. 10 illustrates further assembly of a HIFU transducer of the present invention in which the assembled matching layer 10, composite piezoelectric tiles 40, support frame 50 and printed circuit boards 52 are fit into a circular peripheral frame 80 which is capped with a back plate 70. The back plate 70 thereby encloses an air passageway 76 between the back surfaces of the printed circuit boards 52 and the plate. The back plate includes two air ports 72 and 74, one accessing the cooling space 62' between the center printed circuit board 52' and the center piezoelectric tile through a hole in the board 52', and the other accessing the air passageway 76 between the boards 52 and the plate 70. The back plate 70 is shown in a plan view in FIG. 11. In the example of FIG. 10 the plate 70 contacts the circular central rib of the support frame 50 to separate the cooling space 62' from the peripheral air passageway 76. Air for cooling is forced into one of these ports and out the other to cool the composite piezoelectric tiles 40. It is seen that, unlike a conventional transducer stack, the composite piezoelectric tiles have no backing material attached to their back (non-emitting) surfaces. Instead, they are backed by the cooling space 62. This means that there is no attached backing material to be heated by the composite piezoelectric during use. Instead, the back surface of the composite piezoelectric is cooled by the flow of air in the cooling space 62 between the composite piezoelectric and the printed circuit boards 52. When air is forced into the port 74, for instance, the air will flow through the central cooling space 62', through apertures 64 in the support frame 50 (see FIG. 8), through the cooling spaces 62 between the trapezoidal tiles 40 and the trapezoidal printed circuit boards 52, through the peripheral notches 58 of the printed circuit boards into the air passageway 76, and out through the port 72. Thus, the back surface of the composite piezoelectric tiles can be continuously directly air-cooled during use of the HIFU transducer.

Figure 12:
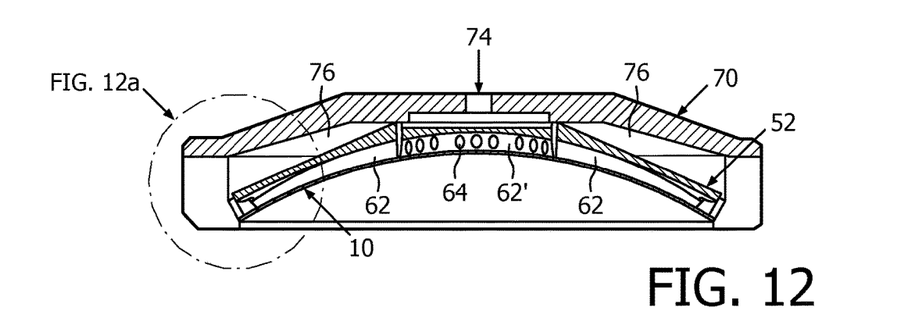
FIG. 12 is a cross-sectional view of the HIFU transducer of FIG. 10.
Figure 12A:
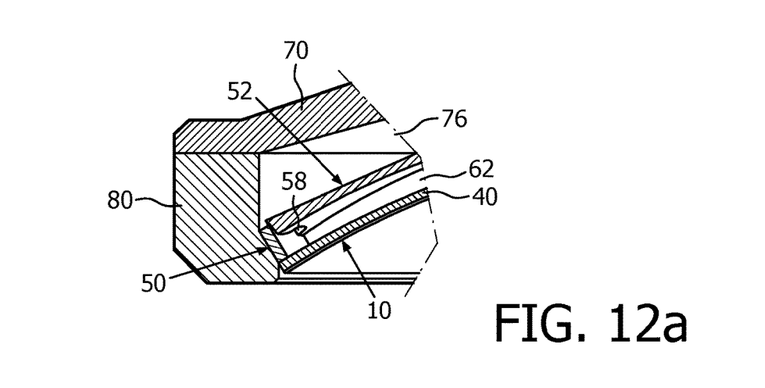
FIG. 12a is an enlarged view of the periphery of the HIFU transducer of FIG. 12.

FIG. 12 is a cross-sectional view through the center of the HIFU transducer assembly of FIG. 10 which further illustrates the elements of the air cooling system of the assembly. FIG. 12a is an enlarged view of the periphery of the assembly, showing a piezoelectric tile 40, support frame 50 and printed circuit board 52 in abutment with the peripheral frame 80 and capped with the back plate 70.

Figure 13:
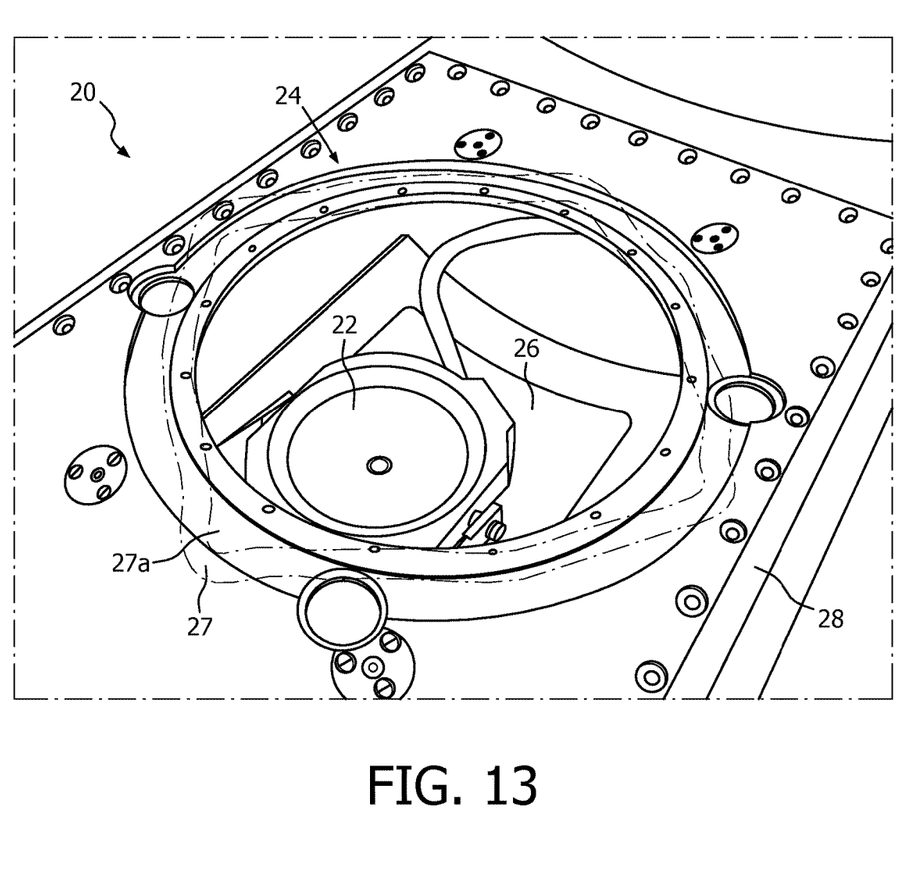
FIG. 13 is a perspective view of a HIFU transducer of the present invention when mounted in a patient support table.

FIG. 13 illustrates a HIFU transducer 22 of the present invention employed in the patient support table 28 of an ultrasonic HIFU system 20. FIG. 13 presents a top view of the patient support table. The patient support table 28 has a first reservoir 24 filled with a suitable transmission liquid, for example, water. For reasons of clarity, the transparent membrane sealing the top of the first reservoir 24 is not shown. The HIFU transducer 22 is located in the first reservoir 24 and is arranged to emit high intensity focused ultrasonic energy upward toward a patient reclined on the table 28. The water of the reservoir 24 provides an acoustic coupling medium between the HIFU transducer 22 and the patient, and also provides cooling of the front of the HIFU transducer. In order to complete the coupling of the ultrasonic energy emanating from the first reservoir to the patient, a second reservoir 27 comprising a low reflective medium is positioned above the first reservoir 24. Preferably, a suitable gel pad is used for the second reservoir. The second reservoir 27 comprises a contact surface 27a onto which a patient to be treated is positioned. The apparatus 20 further comprises an aperture 26 arranged to enable an inspection, for example, a visual inspection, of the contact surface 27a between the second reservoir 27 and the patient. The aperture 26 is preferably arranged as a substantially transparent window through which medical personnel directly, or using a mirror or a suitably arranged camera, can inspect for the presence of air bubbles between the contact surface 27a and the patient. In the case when an air bubble is detected, the patient is repositioned until no air bubbles are present. After that, the patient is suitably immobilized and a treatment may be commenced. The HIFU system 20 of FIG. 13 is further described in international patent application publication number WO 2008/102293 (Bruggers).

What is claimed is:

1. A curved high intensity focused ultrasound (HIFU) transducer comprising:
   a curved piezoelectric array comprising opposite convex and concave surfaces, the concave surface being a transmitting surface, the curved piezoelectric array further comprising a plurality of acoustic transmission areas;
   a plurality of electrodes located on the surfaces of the curved piezoelectric array for applying electrical transmit signals to the acoustic transmission areas; and
   a unitary, continuously formed curved matching layer sheet pre-formed to a desired curvature of the curved transducer array and bonded to the entire transmitting surface of the curved piezoelectric array, thereby providing acoustic matching and electrical isolation for the transmitting surface of the curved piezoelectric array, wherein the curved matching layer includes a convex surface bonded to the transmitting surface of the curved piezoelectric array.

2. The curved HIFU transducer of claim 1, wherein the matching layer further comprises a spherically-curved layer formed by casting or molding.

3. The curved HIFU transducer of claim 2, wherein the spherically-curved layer comprises a convex spherical surface which matches the curvature of the concave surface of the curved piezoelectric array.

4. The curved HIFU transducer of claim 2, wherein the spherically curved layer is cast or molded using a concave molding fixture.

5. The curved HIFU transducer of claim 1, wherein the matching layer further comprises a spherically-curved layer formed by machining a solid matching layer material.

6. The curved HIFU transducer of claim 5, wherein the solid matching layer material is machined to form a convex spherical surface which matches the curvature of the concave surface of the curved piezoelectric array.

7. The curved HIFU transducer of claim 1, wherein the curved matching layer further comprises an epoxy loaded with particles which give the matching layer a desired acoustic property.

8. The curved HIFU transducer of claim 1, wherein the curved matching layer further comprises a thermoplastic resin loaded with particles which give the matching layer a desired acoustic property.

9. The curved HIFU transducer of claim 1, wherein the curved matching layer further comprises a planar sheet of matching layer material which is heated and formed to the desired curvature.

10. The curved HIFU transducer of claim 9, wherein the sheet of matching layer material is heated and formed to exhibit a convex spherical surface which matches the curvature of the concave surface of the curved piezoelectric array.

11. The curved HIFU transducer of claim 1, wherein the curved piezoelectric array further comprises a plurality of piezoelectric tiles which,
   when assembled together, forms the piezoelectric array of the desired curvature; and
   wherein the pre-formed matching layer is coupled to a fixture onto which the piezoelectric tiles are assembled together and bonded.

12. The curved HIFU transducer of claim 11, wherein each piezoelectric tile comprises a partially spherical concave surface,
   wherein the partially spherical concave surfaces conform to a convex surface of the pre-formed matching layer.

13. The curved HIFU transducer of claim 1, wherein the matching layer provides a continuous, moisture-impervious barrier between the curved piezoelectric array and the environment in front of the transducer.

14. The curved HIFU transducer of claim 1, wherein the matching layer further comprises a continuous, electrically-insulating barrier between the curved piezoelectric array and the environment in front of the transducer.

15. The curved HIFU transducer of claim 1, wherein the curved piezoelectric array comprises ceramic piezoelectric material.

16. The curved HIFU transducer of claim 1, wherein the curved piezoelectric array comprises a sheet of material comprising holes configured to provide electrical connection from the concave surface to the convex surface.

17. The curved HIFU transducer of claim 1, wherein the concave surface and the convex surface comprise a conductive material.

18. The curved HIFU transducer of claim 1, wherein the convex surface of the curved matching layer is covered by a metallized electrode.

19. The curved HIFU transducer of claim 11, wherein the plurality of tiles have a trapezoidal shape.

20. A curved high intensity focused ultrasound (HIFU) transducer comprising:
   a curved piezoelectric array comprising opposite convex and concave surfaces, the concave surface being a transmitting surface, the curved piezoelectric array further comprising a plurality of acoustic transmission areas, wherein the curved piezoelectric array comprises a plurality of piezoelectric tiles each of which comprises posts of piezoelectric material embedded in a non-conductive epoxy, and wherein one or more of the posts of each tile includes a via formed therein, the via comprising non-magnetic conductive material;
   a plurality of electrodes located on the surfaces of the curved piezoelectric array for applying electrical transmit signals to the acoustic transmission areas, wherein the plurality of electrodes are provided by metallized layers on the convex and concave surfaces, and wherein the vias formed in the one or more posts connect the metallized layer on the concave surface to the metallized layer on the convex surface; and
   a unitary, continuously formed curved matching layer sheet pre-formed to a desired curvature of the curved transducer array and bonded to the entire transmitting surface of the curved piezoelectric array, thereby providing acoustic matching and electrical isolation for the transmitting surface of the curved piezoelectric array, wherein the curved matching layer includes a convex surface bonded to the transmitting surface of the curved piezoelectric array.

* * * * *